United States Patent [19]

Kojima

[11] Patent Number: 5,233,959
[45] Date of Patent: Aug. 10, 1993

[54] DEVICE FOR CONTROLLING AN IGNITION TIMING FOR AN INTERNAL COMBUSTION ENGINE

[75] Inventor: Sinji Kojima, Himeji, Japan

[73] Assignee: Mitsubishi Denki Kabushiki Kaisha, Tokyo, Japan

[21] Appl. No.: 924,504

[22] Filed: Aug. 4, 1992

[30] Foreign Application Priority Data

Sep. 18, 1991 [JP] Japan .................. 3-238059

[51] Int. Cl.⁵ .............................................. F02P 5/15
[52] U.S. Cl. .................................................. 123/406
[58] Field of Search .............. 123/406, 425, 494; 73/115, 116

[56] References Cited

U.S. PATENT DOCUMENTS

| | | | |
|---|---|---|---|
| 4,485,783 | 12/1984 | Gruden | 123/406 |
| 4,594,982 | 6/1986 | Takahashi et al. | 123/425 |
| 4,854,286 | 8/1989 | Chemnitzer | 123/425 |
| 4,903,663 | 2/1990 | Ooki et al. | 123/425 |
| 4,934,327 | 6/1990 | Hidaka | 123/425 |
| 5,012,782 | 5/1991 | Tokuda | 123/425 |
| 5,050,555 | 9/1991 | Mitsumoto | 123/425 |
| 5,109,821 | 5/1992 | Yoshida et al. | 123/425 |

FOREIGN PATENT DOCUMENTS

| | | | |
|---|---|---|---|
| 0107274 | 5/1987 | Japan | 123/425 |
| 0080071 | 4/1988 | Japan | 123/425 |
| 2-83339 | 6/1990 | Japan . | |

Primary Examiner—Willis R. Wolfe
Attorney, Agent, or Firm—Sughrue, Mion, Zinn, Macpeak & Seas

[57] ABSTRACT

A device for controlling an ignition timing for an internal combustion engine comprising an intake quantity sensor for detecting an intake quantity of an engine; a revolution number sensor for detecting a revolution number of the engine; an ignition timing controlling means for controlling an ignition timing of the engine based on the intake quantity and the revolution number of the engine; a fuel property sensor for detecting fuel property; such as its temperature and whether it is regular or premium gasoline and an ignition timing correcting means for correcting the ignition timing based on the fuel property.

3 Claims, 9 Drawing Sheets

DEVICE FOR CONTROLLING AN IGNITION TIMING FOR AN INTERNAL COMBUSTION ENGINE

BACKGROUND OF THE INVENTION

FIELD OF THE INVENTION

This invention relates to a device for controlling an ignition timing for an internal combustion engine, and particularly to a device for controlling an ignition timing based on fuel property.

DISCUSSION OF THE BACKGROUND

Generally, gasoline on the market is broadly classified into regular gasoline and premium gasoline or high-octane gasoline having a high octane value. FIG. 2(a) shows the relationship between ignition timing and an output torque when regular gasoline and premium gasoline (or high octane gasoline) are utilized. Point A shows a knocking limit when regular gasoline is used, and point B, a knocking limit when premium gasoline is used. When the ignition timing is advanced more than the respective knocking limits, knocking is generated. The more advanced the ignition timing, the more considerable becomes the knocking.

As is apparent in FIG. 2(a), when premium gasoline is used, the ignition timing can be advanced up to point B, thereby increasing the output torque compared with the case wherein regular gasoline is used. FIGS. 2(b) and 2(c) show the knocking limits A and B of the ignition timing with respect to a revolution number and a load of an internal combustion engine. When the revolution number or the load remains the same, the ignition timing can be more advanced by using premium gasoline. Accordingly, an output of an engine can be improved by regulating the ignition timing in accordance with regular gasoline, premium gasoline or a mixture of them for an internal combustion engine.

However, in a conventional device for controlling an ignition timing for an internal combustion engine, a basic ignition timing is set based on either one of regular gasoline and premium gasoline. For instance, in case of a vehicle specified to regular gasoline (wherein the ignition timing is set for regular gasoline), the output of an engine can not be improved simply by using premium gasoline.

SUMMARY OF THE INVENTION

It is an object of the present invention to provide a device for controlling an ignition timing for an internal combustion engine capable of controlling the ignition timing to an optimum value in accordance with the fuel property and capable of promoting a running performance and the output thereof.

According to an aspect of the present invention, there is provided a device for controlling an ignition timing for an internal combustion engine comprising:

an intake quantity sensor for detecting an intake quantity of an engine;

a revolution number sensor for detecting a revolution number of the engine;

an ignition timing controlling means for controlling an ignition timing of the engine based on the intake quantity and the revolution number of the engine;

a fuel property sensor for detecting fuel property; and an ignition timing correcting means for correcting the ignition timing based on the fuel property.

In this invention, the fuel property is detected, and the ignition timing is corrected based on the fuel property.

DETAILED DESCRIPTION OF THE PREFERRED EMBODIMENT

EXAMPLE 1

Figure 1:
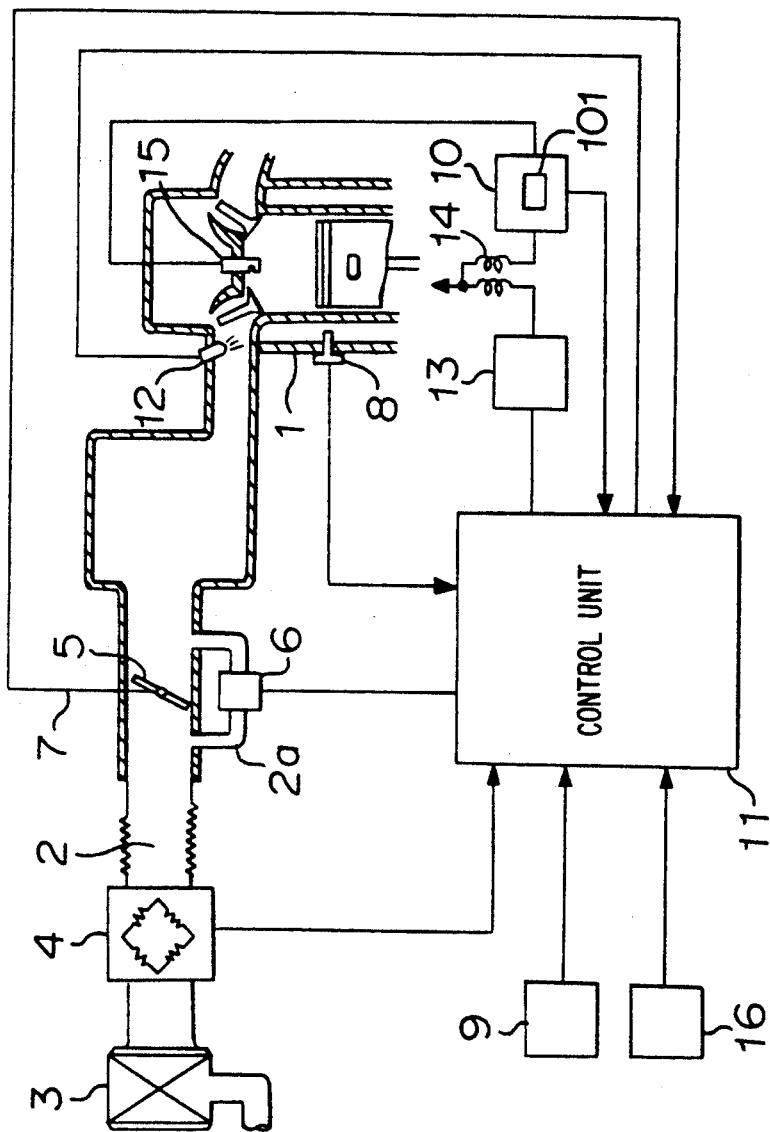
FIG. 1 is a construction diagram of an invented device.
Figure 2A:
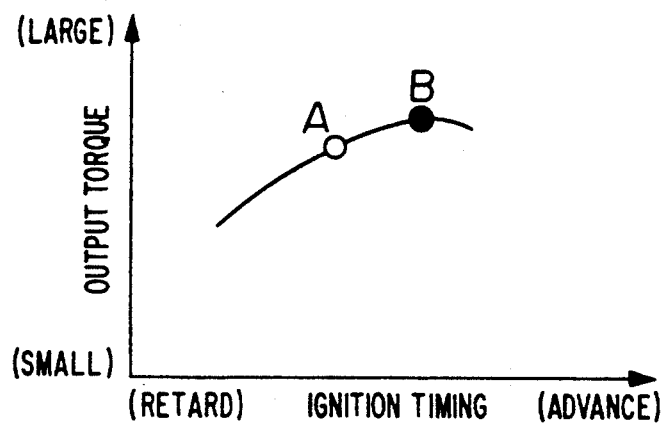
FIGS. 2(a), 2(b) and 2(c) are characteristic diagrams of an engine in accordance with utilized fuels.
Figure 2B:
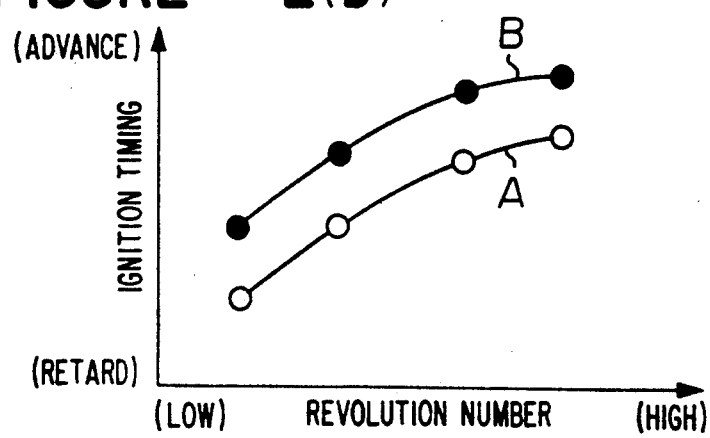
Figure 2C:
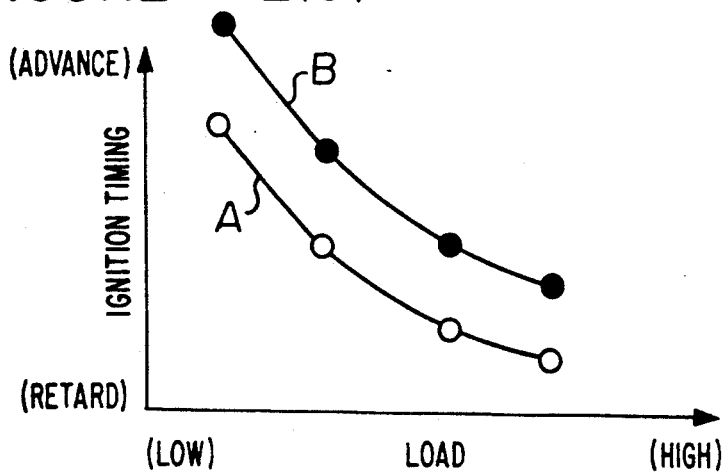

Explanation will be given to an embodiment of the present invention referring to the drawings as follows. FIG. 1 shows construction of the Example of a device for controlling an ignition timing for an internal combustion engine. A reference numeral 1 designates an engine, 2, an intake pipe connected to the engine 1, 3, an air cleaner provided at the entrance of the intake pipe 2, 4, an intake quantity sensor for detecting an intake quantity provided at the intake pipe 2, 5, a throttle valve provided at the intake pipe 2, 2a, a bypass pipe connected to the intake pipe 2 on the upstream and downstream sides of the throttle valve 5, and 6, a bypass control valve provided at the bypass pipe 2a.

Furthermore, a numeral 7 designates a throttle opening degree sensor for detecting an opening degree of the throttle valve 5, 8, a temperature sensor for detecting an engine temperature, 9, a starting switch for detecting a starting state of the engine 1, and 10, a distributor which incorporates a crank angle sensor 101, and which distributes high tension to an ignition plug 15. The crank angle sensor 101 detects a revolution number of the engine 1. A numeral 16 designates a fuel property sensor, which outputs an output signal corresponding to a refractive index of fuel and a fuel temperature signal to a control unit 11. The control unit 11 receives output signals from the respective sensor 4, 7, 8, 16 and 101 and the starting switch 9, performs a fuel control by driving an injector 12, controls a current-flowing time and an ignition timing of an ignition coil 14 by controlling an igniter 13, and performs an idling speed control by driving the bypass control valve 6.

Figure 3:
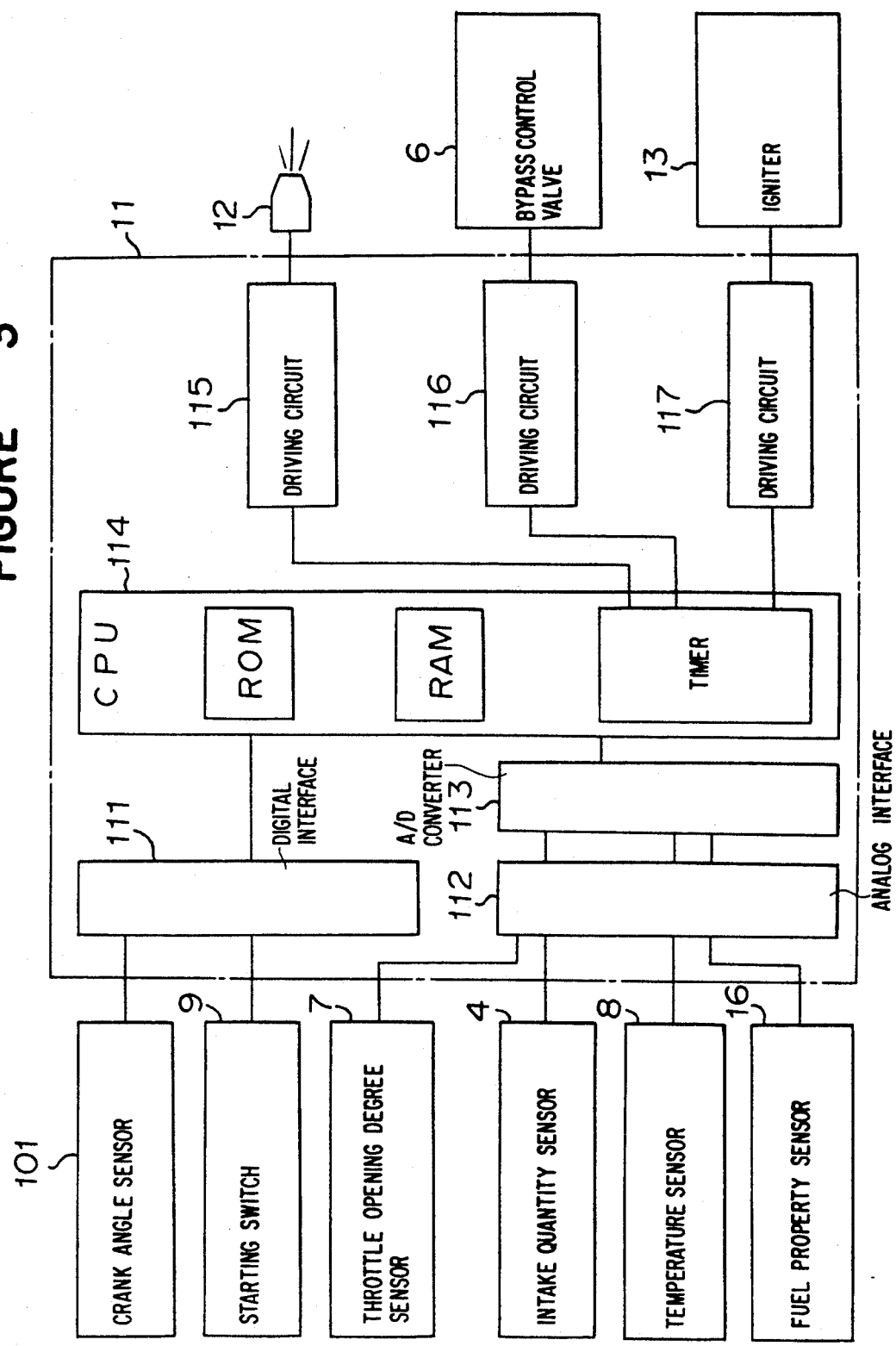
FIG. 3 is a construction diagram of a controlling unit of the invented device.

FIG. 3 shows construction of the control unit 11. A digital interface 111 designates a circuit for inputting digital signals from the crank angle sensor 101, the starting switch 9 and the like to a CPU 114. An analogue interface 112 designates a circuit for inputting analogue signals from the throttle opening degree sensor 7, the intake quantity sensor 4, the temperature sensor 8, the fuel property sensor 16 and the like to an A/D converter 113. The A/D converter 113 A/D-converts the inputs and inputs them to the CPU 114. The CPU 114 incorporates a ROM, a RAM, a timer and the like, and controls driving circuits 115 through 117 based on the above input signals. The driving circuits 115 through 117 respectively drive the injector 12, the bypass control valve 6 and the igniter 13.

Figure 4:
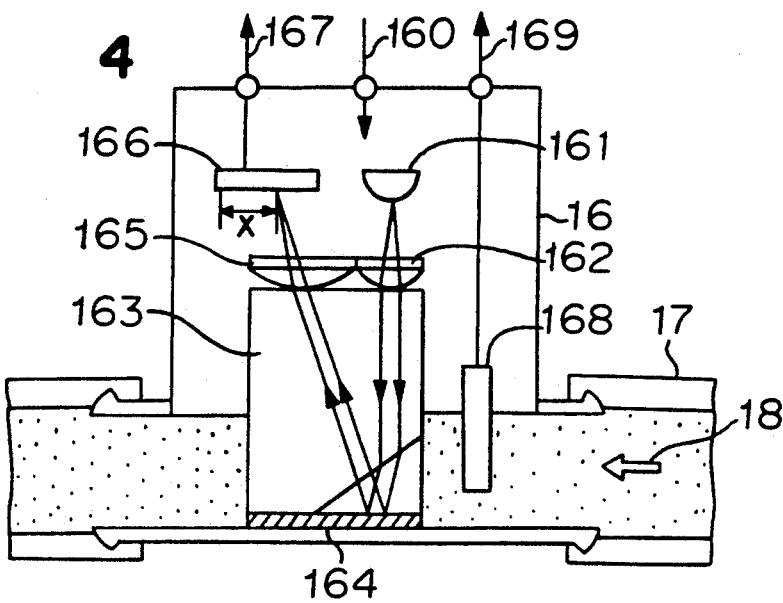
FIG. 4 is a construction diagram of a fuel property sensor in this invention.

FIG. 4 shows the construction of the fuel property sensor 16. The fuel property sensor 16 is provided at a fuel pipe 17. An arrow 18 shows the flow direction of the fuel. A reference numeral 160 designates a power input, 161, a light emitting diode (LED), 162, a collimator lens which converts light from the light emitting diode 161 into parallel rays, and 163, a rod prism. Light passing through the rod prism is refracted on an interface between the rod prism and the fuel in accordance with a ratio between refractive indices of both, reflected by a reflecting mirror 164, refracted on the interface again, and converged on a PSD (one-dimensional position sensing element) 166 by a condenser lens 165.

Accordingly, a converging position of the light is determined on the PSD 166 in accordance with the refractive index of the fuel. A photocurrent of the PSD 166 is converted to a voltage, thereby obtaining an output voltage 167. Furthermore, since the refractive index of the fuel is influenced by the fuel temperature, it is necessary to correct it by the fuel temperature. For that purpose, a fuel temperature sensor 168 is provided in the fuel pipe 17 and a fuel temperature signal 169 is obtained.

Figure 5:
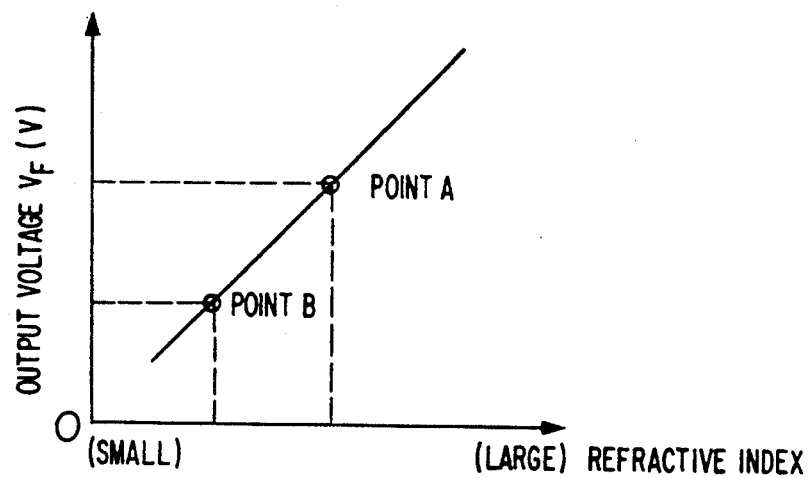
FIG. 5 is an output characteristic diagram of the fuel property sensor.
Figure 6:
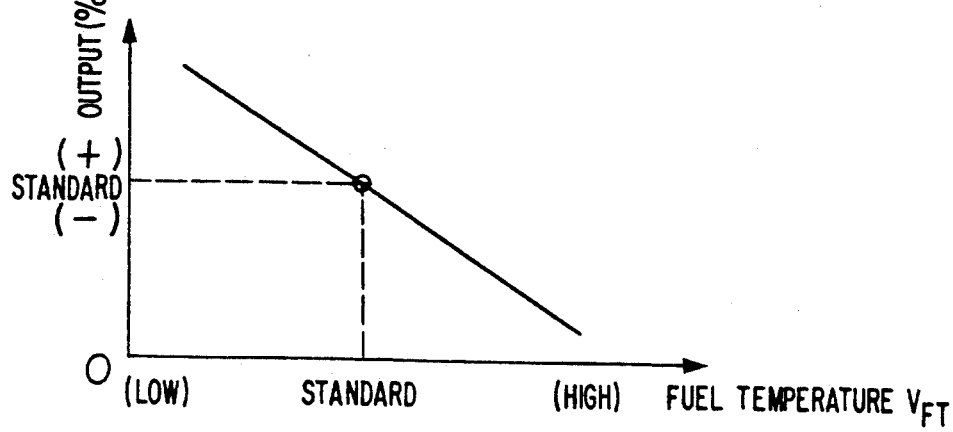
FIG. 6 is a diagram showing a relationship between an output of the fuel property sensor and a fuel temperature according to the present invention.

FIG. 5 shows an output characteristic of the fuel property sensor 16. Point B is for regular gasoline and point A, premium (high-octane) gasoline. The refractive index of fuel is correlated with a specific weight of the fuel, and the specific weight is correlated with an octane-value of the fuel. FIG. 6 shows a relationship between an output of the fuel property sensor 16 and the fuel temperature $V_{FT}$. For instance, when the fuel temperature is higher than a standard value, the output voltage becomes lower that the standard value. Accordingly, by performing an output correction for a difference thereof from the standard value in accordance with the characteristic of FIG. 6, the influence of the fuel temperature can be removed.

Figure 7:
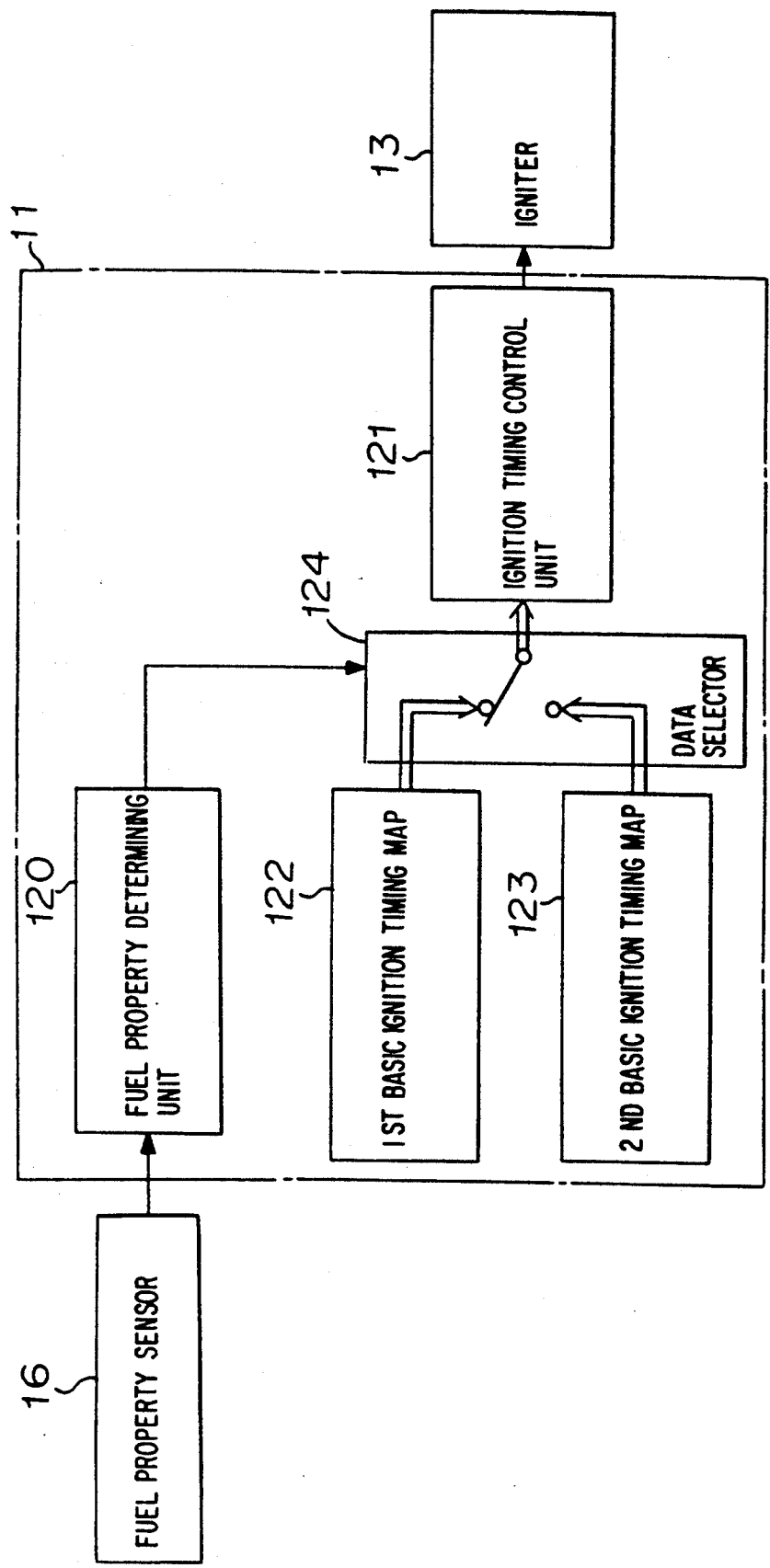
FIG. 7 is a functional block diagram of Example 1 of a control unit of the invented device.

FIG. 7 shows a functional block diagram of the control unit 11. A fuel property determining unit 120 determines the fuel property such as whether a gasoline is regular gasoline or premium gasoline, based on an output of the fuel property sensor 16, and outputs the determination result to a data selector 124. The data selector 124 selects either one of a previously memorized first basic ignition timing map 122 and a previously memorized second basic ignition timing map 123, in accordance with the fuel property. An ignition timing control unit 121 controls the igniter 13 in accordance with the selected basic ignition timing map, and performs an ignition timing control. In this example, for instance, the first basic ignition timing map is for premium gasoline, and the second basic ignition timing map is for regular gasoline.

Figure 8:
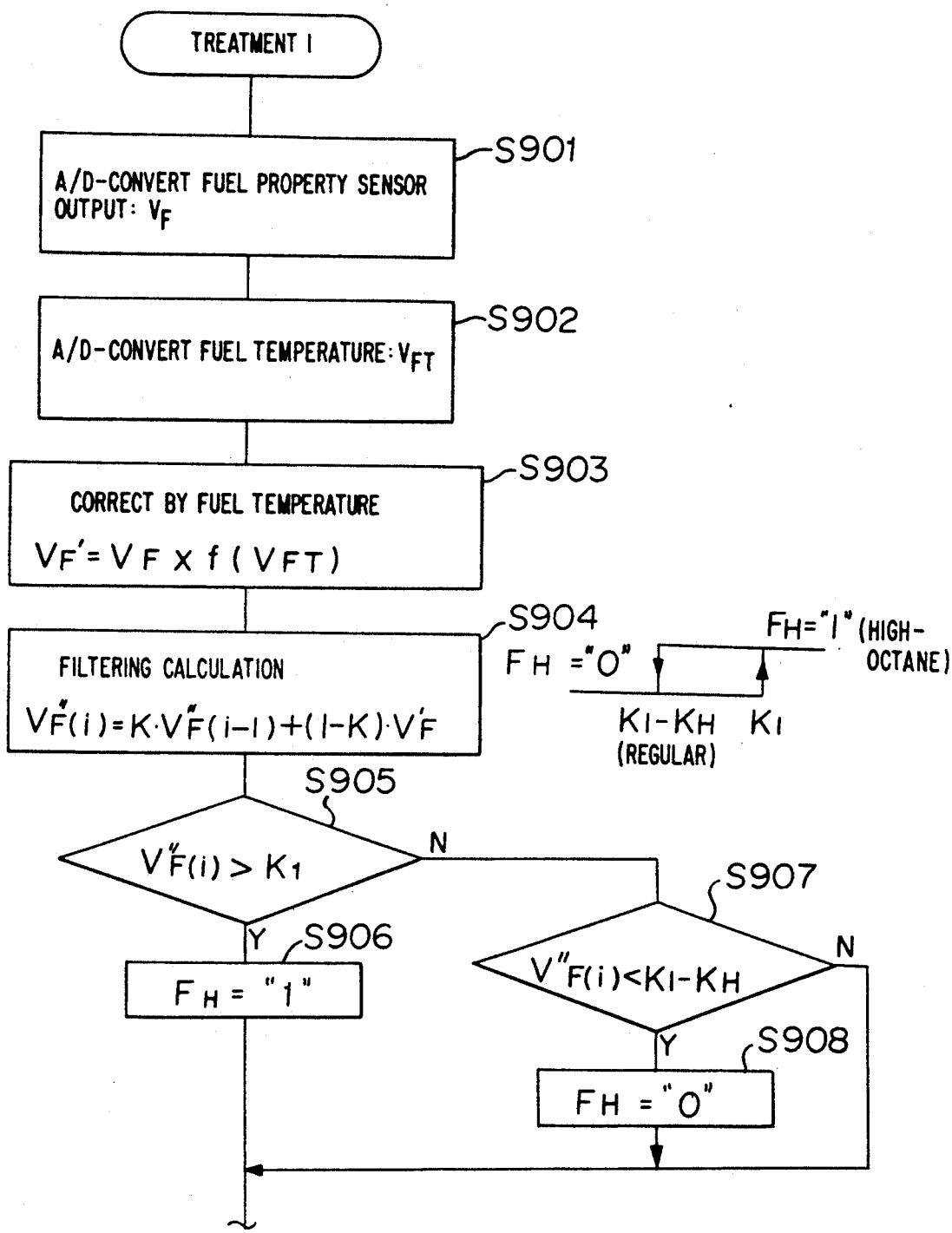
FIG. 8 is a flowchart showing a fuel property determining treatment by the control unit of the invented device.

FIG. 8 shows a treatment for discriminating between a heavy gasoline and a light gasoline by the fuel property sensor 16. In step S901, the operation A/D-converts an output of the fuel property sensor 16, and obtains data $V_F$. Next, in step S902, the operation obtains the fuel temperature from an output of the fuel property sensor 16, and obtains data $V_{FT}$ by A/D-converting the output. In step S903, the Operation corrects the data $V_F$ to an output corresponding to the standard temperature, based on the characteristic of FIG. 6. That is, assuming a corrected value as $V_F'$, $V_F' = V_F \times f(V_{FT})$ Next, in step S904, the operation performs a filtering treatment with respect to the corrected value of $V_F'$. This is to remove a noise with respect to the output, Since the fuel property does not change frequently. The primary filtering treatment is expressed by an equation as follows.

$$V_F''(i) = K V_F''(i-1) + (1-k) \cdot V_F'$$

where K is $0 < K < 1$, and $V_F''$ is an output after the filtering. Next, in step S905, the operation compares $V_F''(i)$ with a criteria $K_1$. When $V_F''(i) > K_1$, the operation determines the gasoline as high-octane gasoline or premium gasoline, and sets a fuel property determining flag $F_H$ as "1" in step S906. If NOT $V_F''(i) > K_1$, in step S907 the operation compares $V_F''(i)$ with $K_1 - K_H$ ($K_H$ is a hysteresis value). When $V_F''(i) < K_1 - K_H$, the Operation determines the gasoline as regular gasoline, and sets the fuel property determining flag as $F_H = $ "0" step S908. When NOT $V_F''(i) < K_1 - K_H$, the operation does not perform the determination. The reason for providing the hysteresis value in the determination, is for stabilizing the operation.

Figure 9:
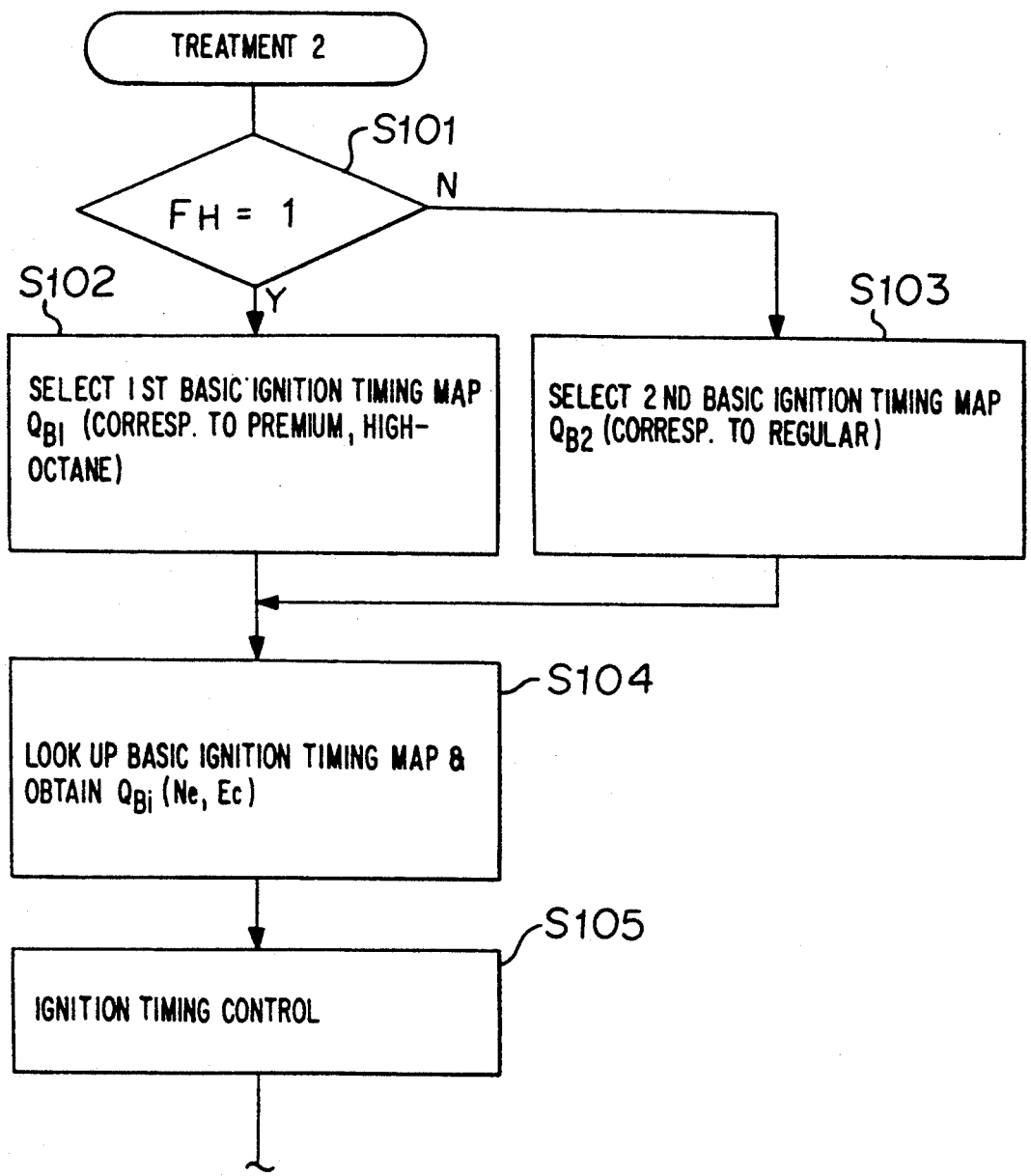
FIG. 9 is a flowchart showing an ignition timing control treatment in the Example 1 of the control unit of the invented device.

FIG. 9 is a flowchart showing the operation of the control unit 11 shown in FIG. 7. In step S101, the operation determines whether $F_H = 1$. When $F_H = 1$, the gasoline is premium gasoline (high-octane gasoline) and the operation selects the first basic ignition timing map $Q_{B1}$ which is optimally matched with respect to premium gasoline (high-octane gasoline), in step S102. In step S104, since the map $Q_{B1}$ corresponds to the engine revolution number $N_e$ and a charging efficiency $E_c$ calculated from the intake quantity, the operation searches the map $Q_{B1}$ by $N_e$ and $E_c$, and obtains a basic advance quantity $Q_{B1}$ ($N_e$, $E_c$). In step S105, the operation performs the ignition timing control based on $Q_{B1}$ ($N_e$, $E_c$).

On the other hand, when $F_H = 0$, Since the gasoline is regular gasoline, the operation proceeds to step S103, and selects the second basic ignition timing map $Q_{B2}$ which is optimally matched with respect to regular gasoline. Similarly, in S104, the operation searches the map $Q_{B2}$, and obtains a basic advance quantity $Q_{B2}$ ($N_e$, $E_c$). In step S105, the operation performs the ignition timing control based on $Q_{B2}$ ($N_e$, $E_c$).

EXAMPLE 2

Figure 10:
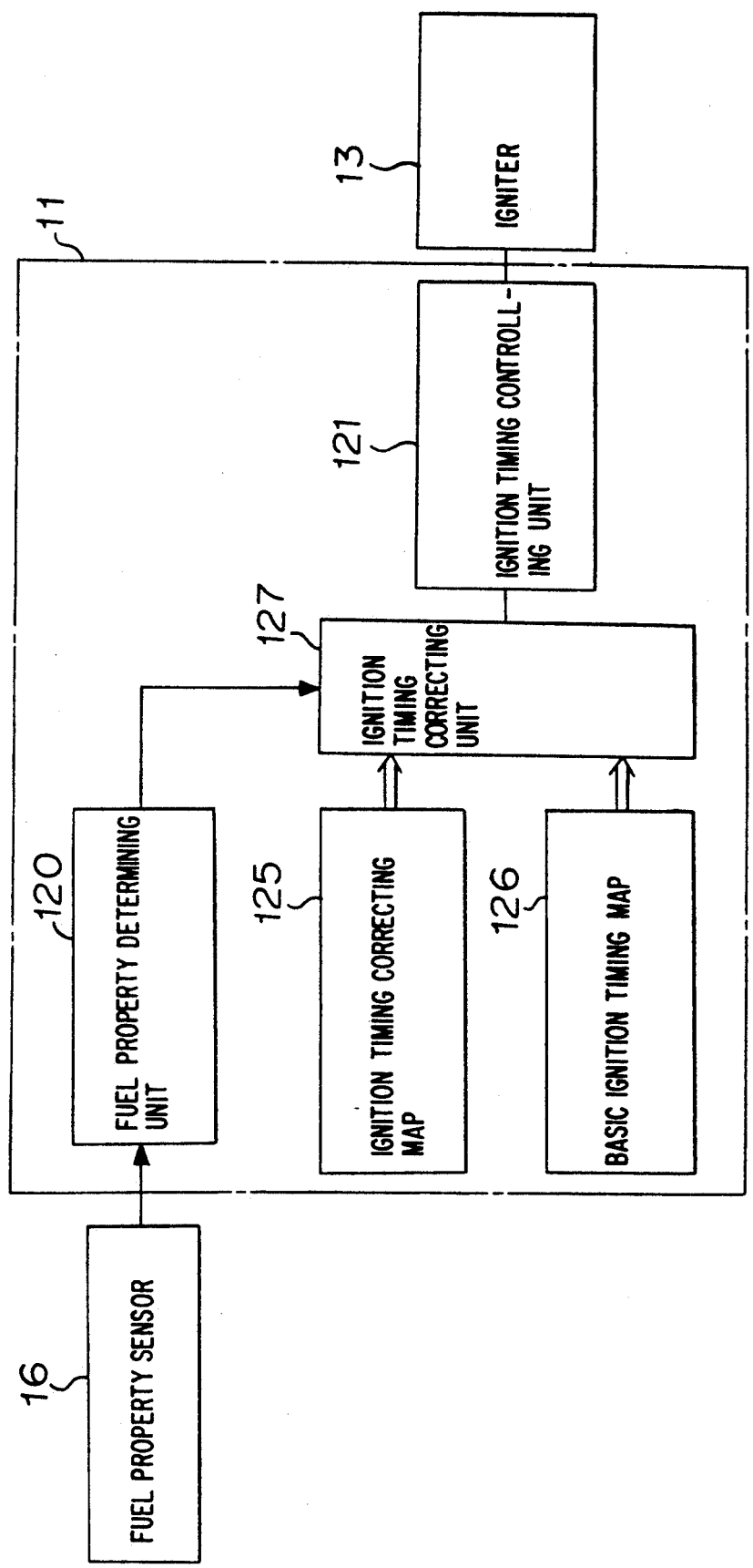
FIG. 10 is a functional block diagram of Example 2 of a control unit of the invented device.

FIG. 10 shows a functional block diagram of the control unit 11 in a second embodiment of the present invention. In FIG. 10, a reference numeral 125 designates an ignition timing correcting map, 126, a basic ignition timing map and 127, an ignition timing correcting unit. The fuel property determining unit 120 determines the fuel property based on an output of the fuel property sensor 16, and outputs the determination result to the ignition timing correcting unit 127. The basic ignition timing map 126 memorizes the ignition timing corresponding with either one of premium gasoline and regular gasoline. When the fuel property corresponds to the basic ignition timing map 126, the ignition timing correcting unit 127 does not perform the correction and the ignition timing control unit 121 controls the igniter 13 in accordance with the basic ignition timing map 126, and performs the ignition timing control. When the basic ignition timing map 126 does not correspond to the fuel property, the ignition timing correcting unit 127 performs the correction based on the ignition timing correcting map 125, and the ignition timing control unit 121 controls the igniter 13 in accordance with the corrected ignition timing.

Figure 11:
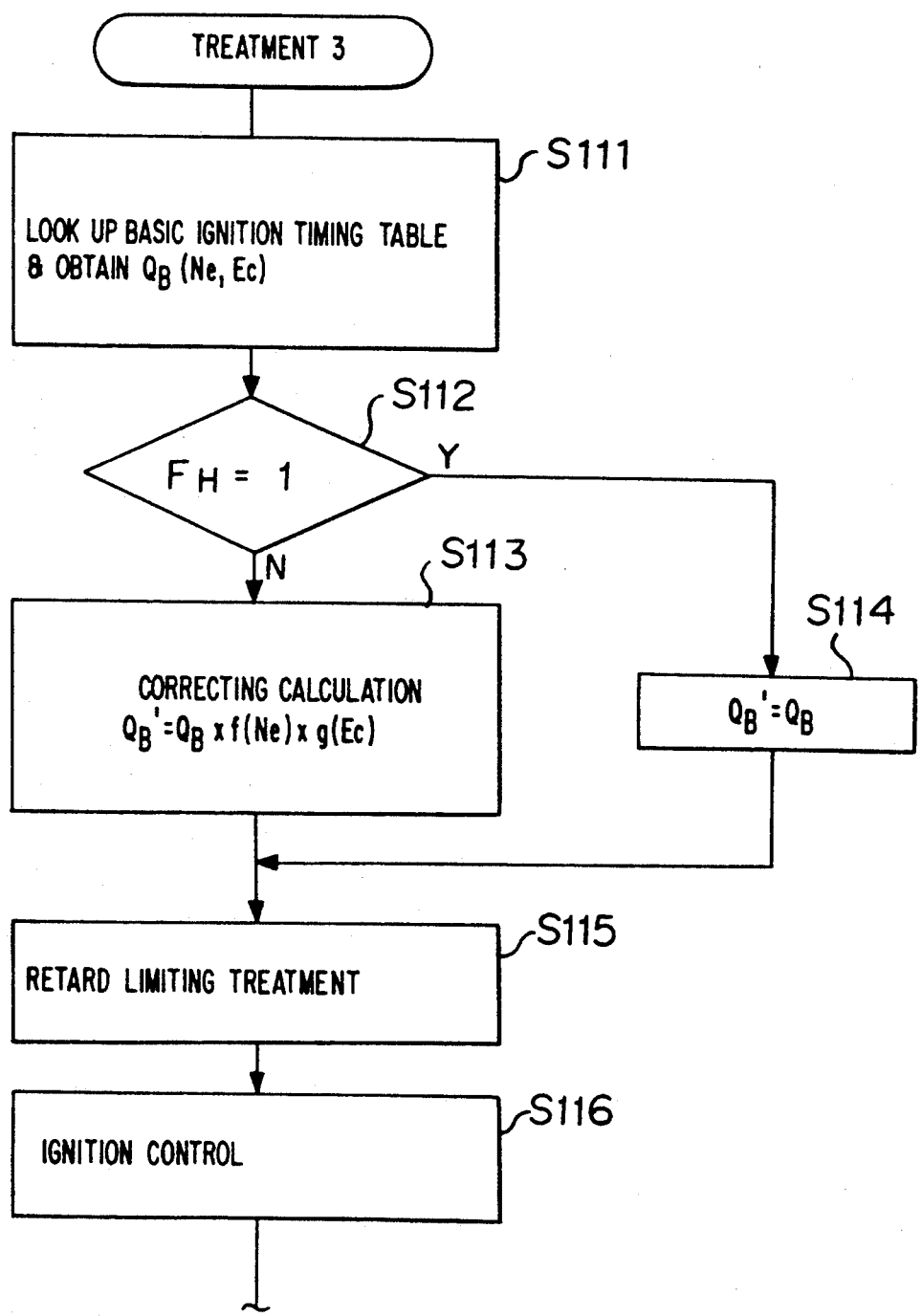
FIG. 11 is a flowchart showing an ignition timing control treatment of Example 2 of the control unit of the invented device.

FIG. 11 is a flowchart for explaining in more detail the operation of the control unit 11 shown in FIG. 10. In this case, explanation will be given to the case wherein the basic ignition timing map 126 is optimally matched with respect to premium (high-octane) gasoline. In step S111, the operation looks up the basic ignition timing map $Q_B$ ($N_e$, $E_c$) by the engine revolution number $N_e$ and the charging efficiency $E_c$ which is obtained by the intake quantity, and obtains the basic ignition timing $Q_B$.

Next in step S112, the operation determines the fuel property by the fuel property determining flange $F_H$. When $F_H=1$, the operation determines the gasoline as premium gasoline, and determines $Q_B'$ as $Q_B'=Q_B$ in step S114 as a treatment without correction. When $F_H=0$, the operation determines the gasoline as regular gasoline, and in step S113, corrects to retard the basic ignition timing $Q_B$ by using the ignition timing correction map 125, and determines the ignition timing $Q_B'$ which is an optimum value with respect to regular gasoline, In this case, the operation obtains a correction coefficient $f(N_e)$ with respect to the engine revolution number $N_e$, and a correction coefficient $g(E_c)$ with respect to the charging efficiency $E_c$ based on the ignition timing correcting map, and performs a correcting calculation of $Q_B'=Q_B \times f(N_e) \times g(E_c)$. Next, in step S115, the operation clips the basic ignition timing by a limit value to avoid too much retard correction. In step S116, the operation controls the igniter 13 based on the ignition timing $Q_B'$. Furthermore, in case that the basic ignition timing map 126 is optimally matched with respect to regular gasoline, when the gasoline is premium gasoline, an advance correction should be made to premium gasoline.

As stated above, according to the present invention, the ignition timing of an engine is controlled in an optimum timing in accordance with the fuel property. Accordingly, the vehicle can obtain good running performance and the output thereof in using any property of a fuel.

What is claimed is:

1. A device for controlling an ignition timing for an internal combustion engine comprising:
   an intake quantity sensor for detecting an intake quantity of an engine;
   a revolution number sensor for detecting a revolution number of the engine;
   an ignition timing controlling means for controlling an ignition timing of the engine based on the intake quantity and the revolution number of the engine;
   a fuel property sensor for detecting a fuel property; and
   an ignition timing correcting means for correcting the ignition timing based on the detected fuel property,
   wherein an output value of the detected fuel property based on the fuel property sensor is corrected in accordance with a difference between a fuel temperature which is detected when the fuel property is detected and a standard fuel temperature.

2. The device for controlling an ignition timing for an internal combustion engine according to claim 1, further comprising: a plurality of ignition timing maps corresponding to the fuel property, means for selecting a suitable one from the plurality of ignition timing maps in accordance with the fuel property, and an ignition timing control unit for performing an ignition timing control based on the selected ignition timing map.

3. A fuel property sensor disposed at a fuel pipe of an internal combustion engine and connected to an ignition timing correcting means comprising:
   a prism immersed in a fuel in the fuel pipe;
   a light emitting element for emitting light to the prism;
   a reflecting element for reflecting the light emitted from the light emitting element which passes through the prism; and
   a position sensing element on which the light reflected by the reflecting element is converged in accordance with refraction thereof in the prism.

* * * * *